US009022783B2

(12) United States Patent
Huwais (10) Patent No.: US 9,022,783 B2
(45) Date of Patent: May 5, 2015

(54) FLUTED OSTEOTOME AND SURGICAL METHOD FOR USE

(75) Inventor: Salah Huwais, Jackson, MI (US)

(73) Assignee: Huwais IP Holding LLC, Jackson, MI (US)

( * ) Notice: Subject to any disclaimer, the term of this patent is extended or adjusted under 35 U.S.C. 154(b) by 126 days.

(21) Appl. No.: 13/427,391

(22) Filed: Mar. 22, 2012

(65) Prior Publication Data

US 2012/0244497 A1    Sep. 27, 2012

Related U.S. Application Data

(60) Provisional application No. 61/466,579, filed on Mar. 23, 2011.

(51) Int. Cl.
*A61C 3/02* (2006.01)
*A61C 8/00* (2006.01)
(Continued)

(52) U.S. Cl.
CPC ........... *A61C 8/0089* (2013.01); *A61B 17/1615* (2013.01); *A61B 17/885* (2013.01); *A61B 17/1604* (2013.01)

(58) Field of Classification Search
CPC ........ A61C 1/003; A61C 1/082; A61C 1/084; A61C 1/186; A61C 3/00; A61C 3/02; A61C 3/06; A61C 8/005; A61C 8/0089; A61C 8/0092; A61B 17/32002; A61B 17/320758; A61B 17/1671; A61B 17/320725; A61B 17/1757; A61B 17/1675; A61B 17/1615; A61B 2217/007; B25H 3/003; B25H 3/006
USPC ........... 433/102, 165–167, 172–173, 215, 76, 433/100, 144, 145; 206/63.5, 379
See application file for complete search history.

(56) References Cited

U.S. PATENT DOCUMENTS

| 3,556,669 A | 1/1971 | Valeska et al. |
| D269,040 S | 5/1983 | Deemer |

(Continued)

FOREIGN PATENT DOCUMENTS

| DE | 102004010859 A | 4/2005 |
| DE | 102004010856 A | 6/2005 |

(Continued)

OTHER PUBLICATIONS

Oxforddictionaries.com. Definition of radial [retrieved on Feb. 25, 2015]. Retrieved from the Internet: http://www.oxforddictionaries.com/us/definition/american_english/radial.*

(Continued)

*Primary Examiner* — Cris L Rodriguez
*Assistant Examiner* — Justin O'Donnell
(74) *Attorney, Agent, or Firm* — Endurance Law Group, PLC (57) ABSTRACT

A surgical method and tool for expanding an initial osteotomy (42) to receive a dental implant (44). An osteotome (22) having a tapered working end (28) is inserted into the initial osteotomy (42). The initial osteotomy (42) is enlarged by simultaneously rotating and pushing the working end (28) of the tapered osteotome (22) into the osteotomy (42). One or more burnishing edges (40) concentrate the pushing and rotational force in outward normal and tangential component forces against the interior surface of the osteotomy (42) to incrementally expand the osteotomy (42) with little to no removal of bone material (46). The inserting and enlarging steps are repeated, as needed, with progressively larger tapered osteotomes (22) until an osteotomy (42) of predetermined size is achieved. Finally, a fixture portion of a dental implant (44) is installed into the expanded osteotomy (42).

17 Claims, 9 Drawing Sheets

(51) Int. Cl.
  *A61B 17/16* (2006.01)
  *A61B 17/88* (2006.01)

(56) References Cited

U.S. PATENT DOCUMENTS

| | | | | |
|---|---|---|---|---|
| 4,474,556 A | * | 10/1984 | Ellis et al. | 433/173 |
| 4,850,867 A | | 7/1989 | Senia et al. | |
| 5,220,964 A | | 6/1993 | Deken et al. | |
| 5,443,468 A | | 8/1995 | Johnson | |
| 5,667,509 A | * | 9/1997 | Westin | 606/80 |
| 5,688,120 A | * | 11/1997 | Yacker et al. | 433/72 |
| 5,735,689 A | | 4/1998 | Mcspadden | |
| 6,146,138 A | | 11/2000 | Dalmau | |
| 6,186,787 B1 | * | 2/2001 | Danger et al. | 433/165 |
| 6,641,395 B2 | | 11/2003 | Kumar et al. | |
| 7,241,144 B2 | | 7/2007 | Nilo et al. | |
| 7,247,020 B2 | * | 7/2007 | Takahashi et al. | 433/165 |
| 7,300,281 B2 | | 11/2007 | Cantatore et al. | |
| 7,402,040 B2 | | 7/2008 | Turri | |
| 7,435,086 B2 | | 10/2008 | Berutti et al. | |
| 7,547,210 B1 | | 6/2009 | Valen | |
| D611,511 S | | 3/2010 | Anitua Aldecoa | |
| 7,766,657 B2 | | 8/2010 | Jaunberzins | |
| 2001/0019816 A1 | * | 9/2001 | Kumar | 433/172 |
| 2002/0094508 A1 | | 7/2002 | Lorenzi | |
| 2005/0123364 A1 | | 6/2005 | Zhou | |
| 2005/0273110 A1 | | 12/2005 | Boehm et al. | |
| 2006/0085005 A1 | * | 4/2006 | Kenealy et al. | 606/80 |
| 2006/0121415 A1 | | 6/2006 | Anitua Aldecoa | |
| 2006/0127847 A1 | | 6/2006 | Danger et al. | |
| 2006/0210949 A1 | * | 9/2006 | Stoop | 433/165 |
| 2007/0037117 A1 | | 2/2007 | Jaunberzins | |
| 2010/0266984 A1 | | 10/2010 | Jung | |
| 2010/0273128 A1 | | 10/2010 | Anitua Aldecoa | |
| 2010/0291511 A1 | | 11/2010 | Lee | |
| 2010/0297578 A1 | | 11/2010 | Jaunberzins | |
| 2012/0244497 A1 | | 9/2012 | Huwais | |
| 2013/0218160 A1 | | 8/2013 | Bjoern et al. | |

FOREIGN PATENT DOCUMENTS

| | | |
|---|---|---|
| DE | 102004010858 A | 6/2005 |
| DE | 102004010860 A | 6/2005 |
| EP | 0379201 A | 7/1990 |
| EP | 2119403 A | 11/2009 |
| FR | 2594684 A | 8/1987 |
| JP | 10217030 A | 8/1998 |
| WO | 2005011514 A | 2/2005 |

OTHER PUBLICATIONS

Anitua, Ridge expansion with motorized expander drills, Implant Dialogue, 14 pgs.
Biohorizons, VIP Catalog and Surgical Manual, 2008, 28 pgs.
Goyal et al., Bone Manipulation Techniques, International Journal of Clinical Implant Dentistry, Jan.-Apr. 2009; 1(1): pp. 22-31.
Lee, Atraumatic Ridge Expansion and Implant Site Preparation with Motorized Bone Expanders, Practical Procedures and Aesthetic Dentistry 2006; 18(1): pp. A-F.
Meisinger, Split-Control, retrieved Mar. 10, 2012 from www.bone-management.com/eng/bm_sortimente_anw_split_eng.htm.
Nishioka, Bone Spreading Technique (Dec. 9, 2010), retrieved Mar. 10, 2012 from www.dentistrytoday.com/implants/4228-bone-spreading-technique, pp. 1-4.
Steier et al., Better horizontal ridge expansion, Dental Tribune I, Sep. 22-28, 2008, pp. 9-10.
Summers, A New Concept in Maxillary Implant Surgery: The Osteotome Technique, Compend Contin Educ Dent, vol. XV, No. 2, pp. 152-160.
Calvo-Guirado JL et al. "Compressive osteotomes for expansion and maxilla sinus floor lifting," Med Oral Patol Oral Cir Bucal 2006;11:E52-5.
www.dentsply-friadent.com, "Ankylos Surgical Manual."
www.nobelbiocare.com, "Validating Innovation: NobelActive Technical and Clinical Story," Nobel Biocare Services AG, 2011.
Biomet Sports Medicine, Bone Dowel Harvester, Copyright 2007, Biomet Sports Medicine, Inc., P.O. Box 587, Warsaw, IN 46581-0587 (www.biometsportsmedicine.com).
Meisinger, Bone Management catalog, pp. 161-178.

* cited by examiner

FLUTED OSTEOTOME AND SURGICAL METHOD FOR USE

CROSS REFERENCE TO RELATED APPLICATIONS

This application claims priority to Provisional Patent Application No. 61/466,579 filed Mar. 23, 2011, the entire disclosure of which is hereby incorporated by reference and relied upon.

BACKGROUND OF THE INVENTION

1. Field of the Invention

The invention relates generally to osteotomes, and more particularly to surgical methods for expanding an initial osteotomy to receive a dental implant.

2. Related Art

Figure 1:
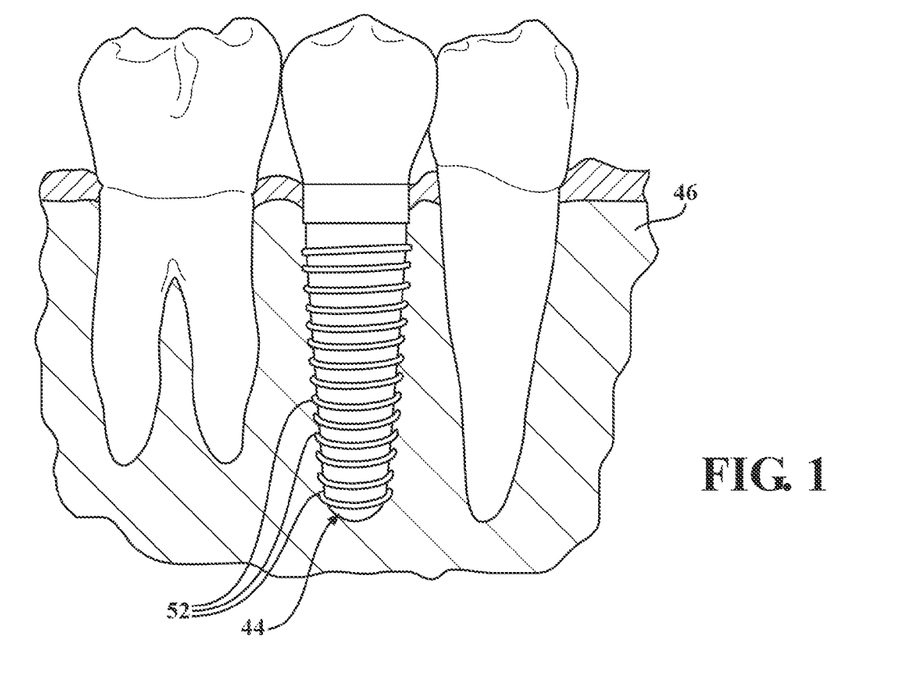
FIG. 1 is a modified cross-sectional view through jawbone showing an exemplary dental implant in bone composed of a lower fixture portion and an upper restoration, the dental implant being flanked on either side by natural teeth.

In its most basic form the placement of a dental implant requires a preparation into the bone using either hand osteotomes or precision drills with highly regulated speed to prevent burning or pressure necrosis of the bone. After a variable amount of time to allow the bone to grow on to the surface of the fixture portion of an implant, a restoration can be placed on the fixture. See for example FIG. 1.

According to current techniques, at edentulous (without teeth) jaw sites that need expansion, a pilot hole is bored into the recipient bone, taking care to avoid the vital structures. The pilot hole is then expanded using progressively wider expander devices (i.e., osteotomes), manually advanced by the surgeon (typically between three and seven successive expanding steps, depending on implant width and length). See for example FIG. 2. Once the receiving hole has been properly prepared, a fixture screw (usually self-tapping) is screwed into place at a precise torque so as not to overload the surrounding bone.

Figure 2:
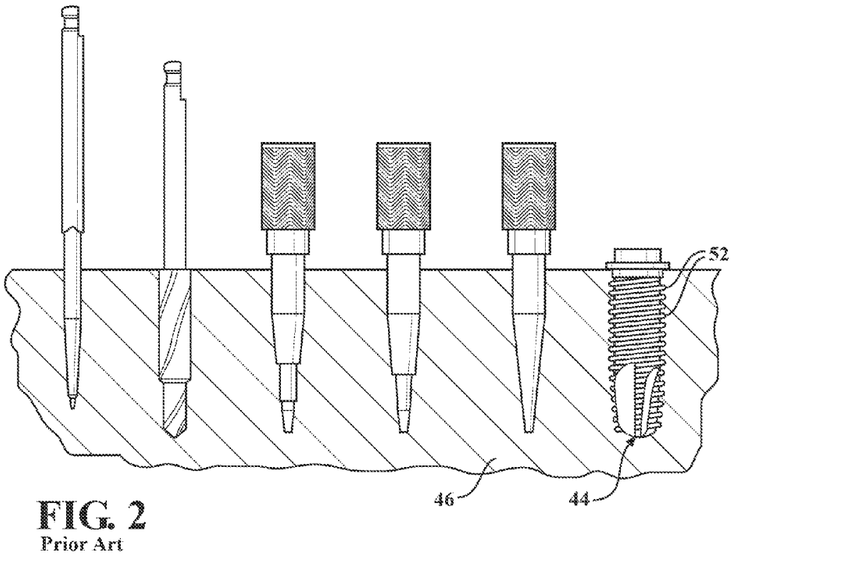
FIG. 2 is a simplified schematic view illustrating a progressive surgical procedure according to the prior art wherein an initial osteotomy is progressively expanded to receive a dental implant using a traditional mallet-driven osteotome technique.

The osteotome technique has become widely utilized in situations requiring ridge expansion. By nature, the osteotome technique is a traumatic procedure. The instruments are advanced with the impact of a surgical mallet, which compacts and expands the bone in the process of preparing osteotomy sites that will allow implant placement. (FIG. 2.) Treatment of mandibular sites is often limited due to the increased density and reduced plasticity exhibited by the bone. Additionally, since the osteotome is inserted by hammering, the explosive nature of the percussive force provides limited control over the expansion process, which often leads to unintentional displacement or fracture of the labial plate of bone. Many patients do not tolerate the osteotome technique well, frequently complaining about the impact from the surgical mallet. In addition, reports have documented the development of a variety of complications that result from the percussive trauma, including vertigo and the eyes may show nystagmus (i.e., constant involuntary cyclical movement of the eyeball in any direction).

More recently, a technique has been developed that allows the atraumatic preparation of implant sites by eliminating the use of a surgical mallet. This procedure is based on the use of a ridge expansion system that includes a bur kit and instruments known as motor-driven bone expanders, such as those marketed by Meisinger split control bone management system (Neuss, Germany). First a pilot hole is drilled at the implant site, then a series of progressively larger expander screw taps are introduced into the bone by hand or with motor-driven rotation, which decreases surgicallrauma (as compared with hammer taps) while providing superior control over the expansion site. See for example FIG. 3. The thread pattern of the expander screw taps has been designed to compact bone laterally as the instrument advances into the osseous crest. This system allows expansion and preparation of implant sites in Type II and III bone, as well as compaction of Type IV bone. The Meisinger split control bone management system may be implemented with a so-called "expander bur" tool to prepare the initial pilot hole to receive the first expander screw tap. In dentistry, the term "bur" is usually synonymous with "cutter." The expander bur tool apparently grinds a taper on the inner wall of the pilot hole osteotomy that will readily accept the tapered shape of the first expander screw tap.

Since they are operated with an electric hand piece, the expander screw taps can be utilized in the anterior as well as posterior regions without impingement of the facial tissues or the positional limitations imposed by traditional osteotomes (unlike a more traditional mallet-driven osteotome which cannot easily reach for example the lower mandible posterior). Furthermore, the rotational control of the expansion permits treatment of the mandibular atrophic ridge. The system can be utilized by itself or with osteotomes and surgical drills to assist in the placement of a variety of implant design.

US Publication No. 2006/0121415 to Anitua Aldecoa describes the use of motor-driven tools and methods for expanding a human bone for the purpose of installing a dental implant. Similar to the progressive illustration shown in FIG. 3, a starter drill is used to create a pilot hole followed by the insertion of an expander screw tap type osteotome having a conical/cylindrical geometry with progressive cross-section. A surgical motor is used to rotate the osteotome at relatively low speeds. Another example of this technique is described in U.S. Pat. No. 7,241,144 to Nilo et al, issued Jul. 10, 2007. The entire disclosures of US Publication No. 2006/0121415 and U.S. Pat. No. 7,241,144 are hereby incorporated by reference.

In the prior art designs involving motor-driven bone expansion, the rotary speed of the expander screw tap is locked in a fixed relationship to the expansion rate of the osteotomy. This is because the expander tap threads cut into the bone and advance the expander tap deeper into the initial osteotomy with rotation. The "root" of the expander screw tap does the expanding work while vertical advance is controlled by pitch of threads and rotation speed. In other words, the thread pitch of the expander screw tap combined with its taper angle is fixed and cannot be altered by the surgeon. If a surgeon wishes to expand the bone more slowly, the only recourse is to turn the expander more slowly. Conversely, if they wish to expand the bone more rapidly, the only option is to turn the expander tool more quickly. Thus, the rate of bone expansion is a direct and unalterable function of the rate at which the surgeon turns the expander tool, and the surgeon is unable to vary other parameters such as pressure and/or rotation rate to achieve an optimum expansion rate.

The utilization of motor-driven bone expanders served in the past (FIG. 3) as an innovative technique offering an atraumatic alternative to the traditional mallet-driven osteotomes (FIG. 2). These instruments also provide, at least arguably, a favorable increase in the control of the bone expansion, which facilitates implant-site preparation while allowing universal intraoral use. Nevertheless, there are many shortcomings of the present motor-driven bone expander screw tap techniques. These shortcomings include a relatively large number of intermediate progressive expansions steps due to the surgeon's inability to disassociate the tool rotation rate from the bone expansion rate. Thus, a typical osteotomy kit may include 4-6 expander screw taps which make the kit cost relatively expensive. Another disadvantage is that each expander screw tap takes time to install and perhaps an equal amount of time to remove (i.e., un-screw). Because of the relatively large number of progressive expansions steps needed, this translates to a long surgical procedure which increases patient discomfort and procedure cost. Yet another disadvantage is that each rotary expansion step introduces some degree of error into the osteotomy. The surgeon's hand controlling the advancing expander screw tap is typically located outside the patient's mouth, which is laterally offset from the rotational axis of the expander tap. Thus, even though a surgical motor may be used to drive the expander tap, there is a very real possibility that the surgeon will introduce the some tilt or wobble inadvertently as the expander tap is advanced (or withdrawn) thus distorting the intended shape of the osteotomy or even worse provoking a lateral fracture in the bone.

This inexorable linking of tool rotation rate to bone expansion rate in all prior art rotary expander systems limits surgical control over the implant process, and in some cases may lead to unnecessary patient discomfort. There is therefore a need in the art for an improved surgical method for expanding an initial osteotomy to receive a dental implant, and tools therefor, that provide greater surgical control, are less costly, less likely to introduce error and that reduce patient discomfort.

SUMMARY OF THE INVENTION

This invention contemplates a surgical method for expanding an initial osteotomy to receive a dental implant. An osteotome is provided having a tapered working end. The tapered working end of the osteotome is inserted into an initial osteotomy. The initial osteotomy has an interior surface surrounded by bone. The initial osteotomy is enlarged by forcibly advancing the osteotome into the initial osteotomy. The inserting and enlarging steps are repeated, as needed, with progressively larger tapered osteotomes until an osteotomy of predetermined size is achieved. Finally, a fixture portion of a dental implant is installed into the expanded osteotomy. The invention is distinguished by the working end of the tapered osteotome having one or more longitudinally extending burnishing edges. The enlarging step includes simultaneously rotating and pushing the working end of the tapered osteotome into the osteotomy so that the one or more burnishing edges concentrate the pushing and rotational force through the burnishing edge in outward normal and tangential component forces against the interior surface of the osteotomy to incrementally expand the osteotomy with little to no removal of bone material.

Burnishing is the deformation of a surface due to stressed contact with another object. Burnishing is commonly used in metalworking as a cold forming process, without actual removal of metal, where a tool is rubbed on the metal surface of the part with sufficient force to cause plastic flowing of the metal. The technique of burnishing is not commonly applied in the dental arts, and is heretofore not been applied in surgical procedures to expand an initial osteotomy for the purpose of receiving a dental implant.

According to another aspect of this invention, a burnishing osteotome is provided comprising a longitudinally extending shank and a working end. The shank has a coupling at one end thereof, and the working end extends longitudinally from the shank opposite the coupling. The working end has a taper along its length. The working end includes a root shaft. A plurality of flutes extend from the root shaft. Each the flute extends radially outwardly to a crest. Due to the taper, the crest defines the major diameter of the working end as a function of length. A longitudinally extending burnishing edge is disposed along each crest. The burnishing edge is non-rotatably fixed relative to the root shaft, and is defined by a large negative rake angle.

This invention overcomes the disadvantages and shortcomings of prior art osteotome techniques offering an atraumatic alternative to the traditional mallet-driven osteotomes without any disadvantages of rotary expander screw tap systems. The present surgical method and accompanying surgical tool for implementing the method provides a highly controllable, relatively fast and effective technique for expanding an initial osteotomy to receive a dental implant. By forcibly rubbing the burnishing edges of the osteotome against the interior surfaces of the osteotomy, the bone material is effectively expanded and simultaneously compressed without creating excessive heat or trauma to the bone material. Because the concepts of this invention de-link rotation rate of the tool to the bone expansion rate, the surgeon is provided with substantially greater control which reduces the possibility for the introduction of inadvertent lateral forces prevalent with prior art expander screw tap devices. Surgical procedures according to the present methods can be carried out over less time, thereby resulting in less trauma and discomfort for the patient.

BRIEF DESCRIPTION OF THE DRAWINGS

These and other features and advantages of the present invention will become more readily appreciated when considered in connection with the following detailed description and appended drawings, wherein.

DETAILED DESCRIPTION OF THE PREFERRED EMBODIMENT

Referring to the figures wherein like numerals indicate like or corresponding parts throughout the several views, a burnishing osteotome according to the present invention is generally shown at 22 in FIGS. 4-11 and 13. The osteotome 22 comprises a longitudinally extending shank 24. The shank 24 has a coupling 26 at one end thereof to attach to a rotary input such as from a surgical motor having speed and torque controls. The osteotome 22 also includes a working end 28. The working end 28 extends longitudinally from the shank 24 opposite the coupling 26, and has a length of approximately 11-15 mm, although longer or shorter lengths may also be fashioned to suit the application. As perhaps best shown in FIG. 5, the working end 28 has a taper along at least a portion of its length. A leading distal tip 30 of the working end 28 defines a minimal outer diameter, and an upper end 32 defines a maximum outer diameter of the tapered portion. The difference between the minimal outer diameter (at 30) and the maximum outer diameter (at 32) is preferably 1 mm, although larger or smaller differences can be achieved with larger or smaller taper angles.

Figures 5, 6:
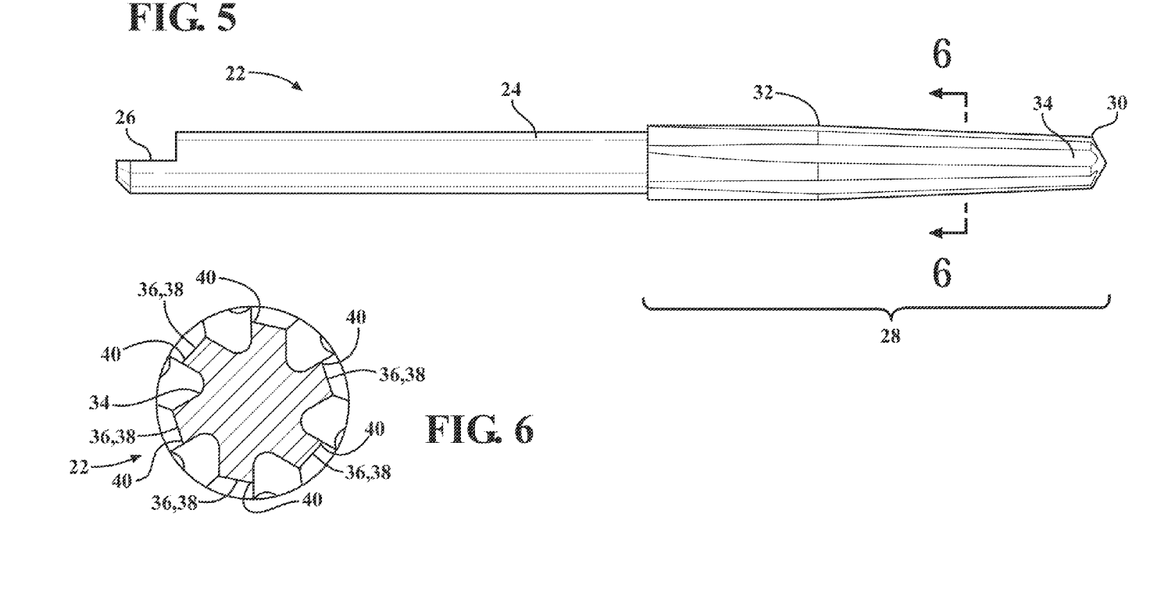
FIG. 5 is a side elevation view of the osteotome shown in FIG. 4.
FIG. 6 is a cross-sectional view through the working end of the osteotome as taken generally along lines 6-6 in FIG. 5.
Figure 7:
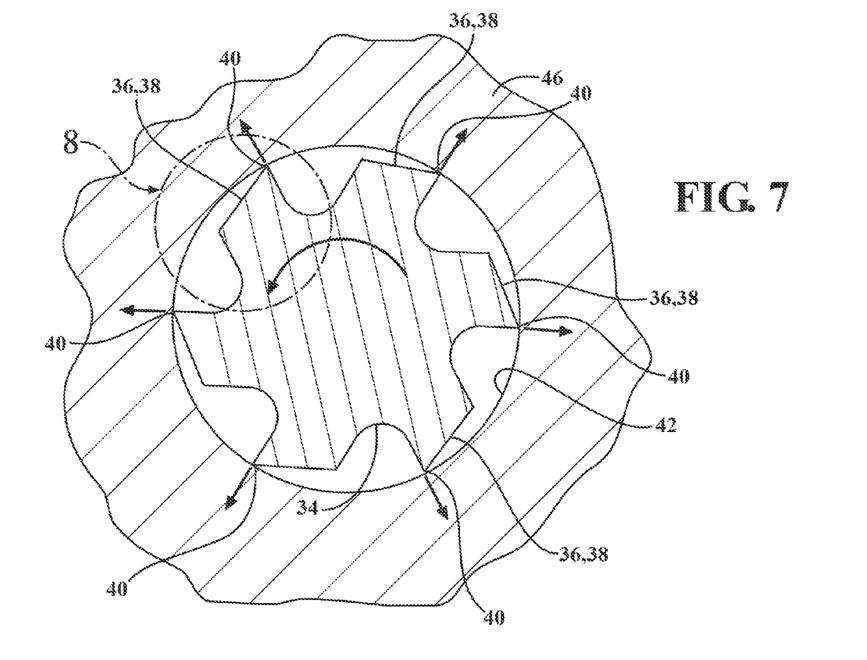
FIG. 7 is a cross-sectional view through the working end of an osteotome as taken generally along lines 6-6 in FIG. 5 but looking the other direction which, in use, is downwardly into an osteotomy, with radial lines emanating from the burnishing edges of the osteotome to indicate laterally outward expansive forces applied through the burnishing edges to the interior surface of an osteotomy.

Referring now to the cross-sectional views of FIGS. 6 and 7, the working end 28 is shown including a root shaft 34, from which at least one, but more preferably a plurality of flutes 36 extend. The plurality of flutes 36 may comprise at least three flutes 36. Preferably, the plurality of flutes 36 are equally circumferentially spaced from one another so that if there are four flutes 36 they are arranged 90° apart; six flutes 36 would be arranged 60° apart; eight flutes 36 would be arranged 45° apart; ten flutes 36 would be arranged 36° apart; and so on.

Each flute 36 extends radially outwardly to a crest 38 which defines the major diameter of the working end 28 as a function of length. That is, because the working end 28 is tapered, its diameter changes along its length. Therefore the major diameter adjacent the distal tip 30 will be smaller than the major diameter adjacent the upper end 32. Thus, the major diameter is a function of length measured as it were from the distal tip 30. As perhaps best shown in FIG. 8, a longitudinally extending burnishing edge 40 is disposed along the outermost portion of the crest 38. Thus, the burnishing edge 40 is that specific portion of the crest 38 which lies along the major diameter of the tapered working end 28. In the embodiments illustrated in the drawing figures, the burnishing edge 40 in each instance is non-rotatably fixed relative to the root shaft 34. This is due in large part to manufacturing constraints for the relatively small osteotome sizes. However, if manufacturing techniques permitted, the burnishing edge 40 could be formed by a roller element in order to reduce friction and better manage heat build-up.

Returning again to FIG. 8, the crest 38 is shown as establishing a large negative rake angle leading up to the burnishing edge 40. A rake is an angle of slope measured from the leading face of the tool (the crest 38 in this case) to an imaginary line extending perpendicular to the surface of the worked object (e.g., inner bone surface of the osteotomy). Rake angle is a parameter used in various cutting and machining processes, describing the angle of the cutting face relative to the work. There are three types of rake angles used in metal working: positive, negative, and zero. However, in the preferred embodiment of this present application of a burnishing technique, a negative rake angle is employed, and more preferably a large negative rake angle. While the actual angle of the negative rake is adaptable to suit the particular specifications, including the relative roundness or sharpness of the burnishing edge 40, negative rake angles greater than about 45°, and even more preferably greater than 60°, have been found to produce satisfactory results. The large negative rake angle of the present osteotome 22 applies outward pressure at the burnishing edge 40 to create a compression wave ahead of the point of contact, loosely akin to spreading butter on toast. Downward pressure applied by the surgeon is needed to keep the burnishing edge 40 in contact with the bone surface of the osteotomy being expanded, that is, to keep it pushing on the compression wave. This is aided by the taper effect of the osteotomy and tool 22 to create lateral pressure (i.e., in the intended direction of expansion). The harder the surgeon pushes down, the more pressure is exerted laterally. This gives the surgeon complete control of the expansion rate irrespective to a large degree on the rotation speed of the osteotome 22. Thus, the burnishing effect's intensity depends on the amount of force exerted on the osteotome 22. The more force exerted, the quicker expansion will occur. The burnishing edges 40 along the respective crests 38 of the flutes 36 lap against bone and do the expanding work as the osteotome 22 is rotated in combination with downward pressure applied by the surgeon.

Figure 8:
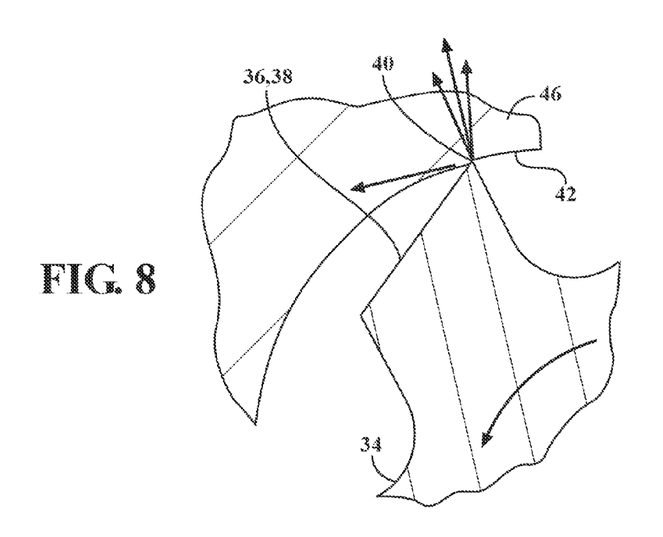
FIG. 8 is an enlarged view of the area circumscribed at 8 in FIG. 7 and depicting the interaction between the burnishing edge of the flute of the osteotome and the interior surface of the osteotomy, with radial and longitudinal forces indicated by arrows.

As shown in the enlarged and somewhat exaggerated for clarity FIG. 8, as the burnishing edge 40 drags across the bone, the force on the burnishing edge 40 can be decomposed into two component forces: one normal to the bone's surface, pressing it outwardly, and the other tangential, dragging it along the inner surface of the osteotomy. As the tangential component is increased, the burnishing edge 40 will start to slide along the bone. At the same time, the normal force will deform the softer bone material. If the normal force is low, the burnishing edge 40 will rub against the bone but not permanently alter its surface. The rubbing action will create friction and heat, but this can be controlled by the surgeon by altering, on-the-fly, the rotation speed and/or pressure and/or irrigation flow. As will be described subsequently in connection with FIG. 20, because the working end 28 of the osteotome 22 is tapered, the surgeon may at any instant during the surgical procedure lift the burnishing edges 40 away from contact with the surface of the bone to allow air cooling or irrigation. This can be done in a controlled "bouncing," i.e., axially reciprocating, fashion where pressure is applied in short bursts with the surgeon continuously monitoring progress and making fine corrections and adjustments. Conversely, as the normal force increases, eventually the stresses in the bone's surface exceed its yield strength. When this happens, the burnishing edge 40 will plow through the surface and create a trough behind it. The plowing action of the burnishing edge 40 thus progressively enlarges the osteotomy. While the elastic properties of bone are well-known, if the load imposed exceeds the bone's ability to deform elastically, it will deform further and change shape permanently by plastic deformation. The permanent change in shape is believed to be associated with micro-cracks that allow energy release, a compromise that is a natural defense against complete fracture. If these micro-cracks are small, the bone remains in one piece while the osteotomy expands.

Said another way, expansion of the osteotomy occurs when the burnishing edge 40 is rotated against the bone surface of the osteotomy and downward pressure is applied by the surgeon. This has the effect of causing, at the same time, rotation and translation of the burnishing edge 40, but in a manner that does not positively link rotation and translation as in prior art expander screw tap devices. The osteotomy, therefore, is formed into the final size ready to receive the fixture portion of a dental implant by a series of small incremental plastic deformations created by sweeps of successive burnishing edges 40 pressed hard against the interior surface of the osteotomy. Each such plastic deformation is followed by a short interval of rest before the arrival of the next successive burnishing edge 40.

The burnishing edge 40 is shown in as comprising a chisel-like shape held at the previously described large negative rake angle. However, those of skill will appreciate that the burnishing edge 40 could be formed by other crest 38 profile shapes, such as rounded or lobed designs, provided the manufacturing techniques required to make such an alternative profile were found to be cost-justified in comparison with that of the preferred profile as shown in FIGS. 7 and 8.

Figure 9:
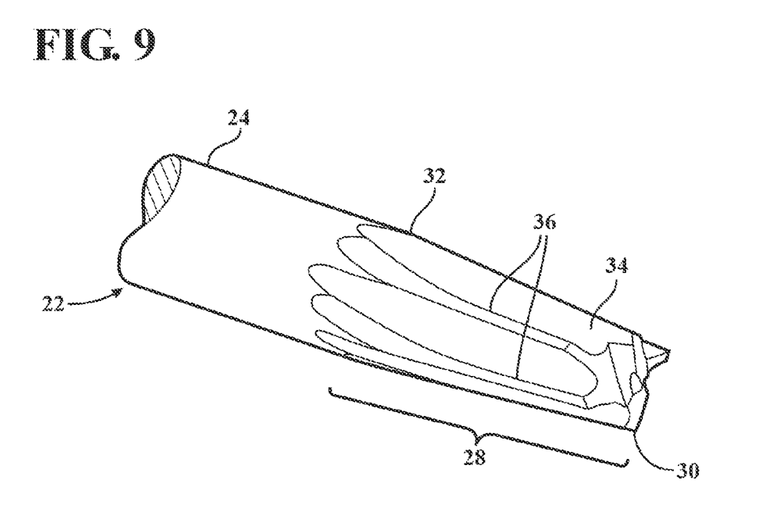
FIG. 9 is a fragmentary perspective view showing the working end of an osteotome according to one embodiment of this invention having six straight flutes.
Figure 10:
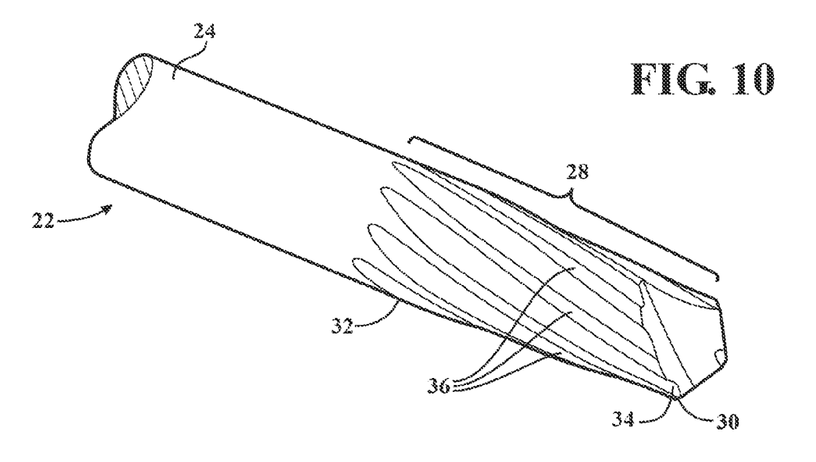
FIG. 10 is a fragmentary perspective view of an alternative osteotome configuration according to this invention wherein the working end is configured with ten spiral flutes.
Figure 11:
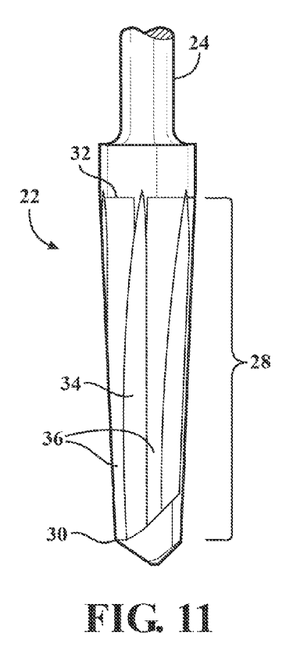
FIG. 11 is a front elevation view of an osteotome embodiment according to this invention including six straight flutes.
Figure 12:
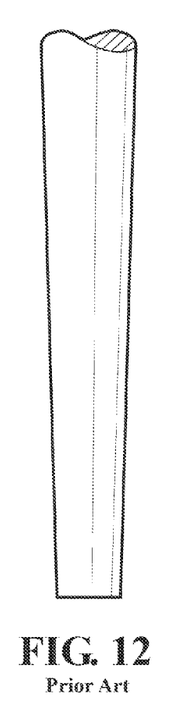
FIG. 12 is a front elevation view of a prior art osteotome of the mallet-driven type shown for comparison purposes adjacent to the osteotome of FIG. 11.
Figure 13:
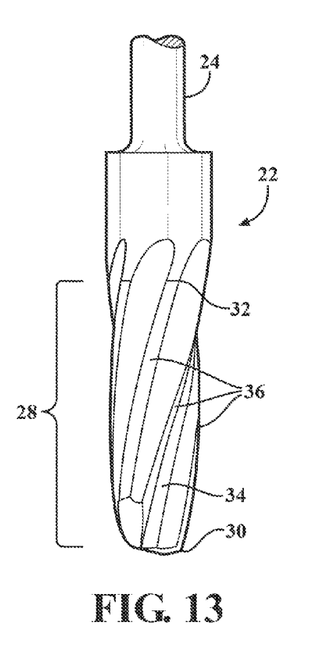
FIG. 13 is a front elevation view of an alternative embodiment of an osteotome according to the subject invention including six helically spiraling flutes shown for comparison purposes adjacent the prior art osteotome of FIG. 12.

Turning now to FIGS. 9-13, the illustrations depict various embodiment in which the flutes 36, and thus by extension the burnishing edges 40, may be formed either with no twist, i.e., straight as in FIGS. 9 and 11, or with a spiral twist along the length of the working end 28 as in FIGS. 10 and 13. A prior art osteotome of the mallet-driven type is shown for side-by-side comparison purposes in FIG. 12.

Figure 14A:
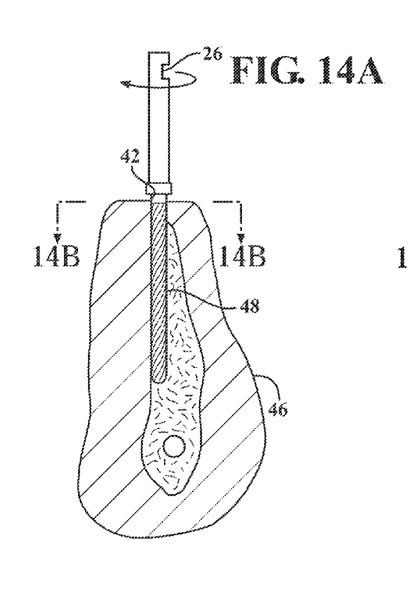
FIG. 14A is a simplified cross-sectional view through a bone prepared for surgical expansion with a pilot drill having created an initial osteotomy site.
Figure 14B:
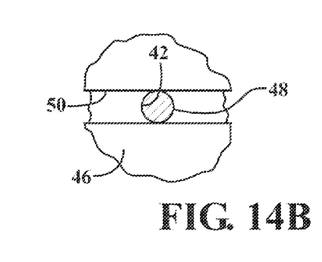
FIG. 14B is a view taken generally along lines 14B-14B in FIG. 14A.

Turning now to FIGS. 14A-20, surgical methods are depicted for expanding an initial osteotomy 42 to receive a dental implant 44. Typically as a first step an initial osteotomy site is prepared by exposing bone 46, and then drilling a pilot hole into the bone 46 with a pilot drill 48. This is shown in FIG. 14A, and may be accomplished with a typical prior art surgical pilot drill 48 turned in a standard clock wise direction. The pilot hole in this instance comprises the initial osteotomy 42. In some cases, the surgeon may decide it is beneficial to saw a groove 50 along the bone ridge as seen in FIG. 14B. The sawed groove 50 typically intersects the pilot hole 42 along the ridge of the bone 46. The surgeon may decide to first drill the pilot hole and then saw the groove 50, or vice versa.

A first osteotome 22 according to the present invention is operatively connected to a surgical motor (not shown) though its coupling 26 feature. Then the working end 28 of the first osteotome 22 is inserted into an initial osteotomy 42. The interior surface of the initial osteotomy 42 is surrounded by bone 46. If the diameter of the pilot drill 48 is, for example 1.5 mm, then preferably the major diameter of the working end 28 of the first osteotome 22 adjacent the leading distal tip 30 is also 1.5 mm so that it follows easily the pilot hole. Because of the widening taper, the major diameter of the working end 28 adjacent upper end 32 is larger than the initial osteotomy. This may be, for example, 2.5 mm. At these exemplary dimensions, a first osteotome 22 having six equally spaced flutes 36/burnishing edges 40 of straight or helical twist has been found to provide satisfactory results. More or fewer flutes 36/burnishing edges 40 are certainly possible.

Figure 15A:
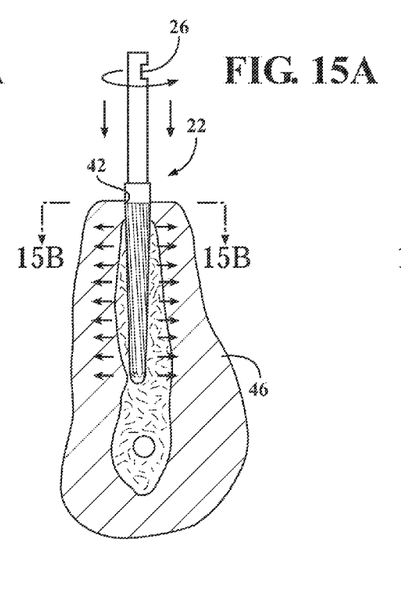
FIG. 15A is a simplified surgical procedure showing a progression from that of FIG. 14A with a first osteotome having been inserted into the initial osteotomy to expand the initial osteotomy into a first expanded osteotomy.
Figure 15B:
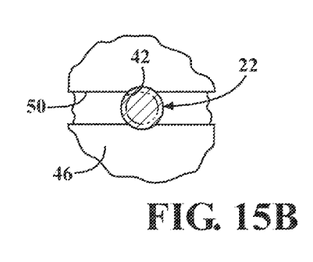
FIG. 15B is a view taken generally along lines 15B-15B of FIG. 15A.

The initial osteotomy 42 is enlarged in a next step of the procedure by forcibly advancing the working end 28 of the first osteotome 22 into the initial osteotomy 42, which is depicted in FIG. 15A. This forcible advancing includes simultaneously rotating and pushing the working end 28 of the first tapered osteotome 22 into the osteotomy 42 so that its one or more burnishing edges 40 concentrate the pushing and rotational force in outward normal and tangential component forces (FIG. 8) against the interior surface of the osteotomy 42. FIG. 15A illustrates a counter-clockwise rotation of the osteotome 22, but that direction is merely preferred and can be reversed with suitable alterations made to the shape of the osteotome 22. Although the surgeon may vary the rotational speed of the osteotome 22 according to the dictates of the situation in their judgment, experimental results indicate that rotation speeds greater than about 200 RPM and torque settings greater than about 15 Ncm provide satisfactory results. More preferably rotation speeds greater than about 600 RPM and torque settings greater than about 20 Ncm provide satisfactory results. And still more preferably, rotation speeds in the range of 800-900 RPM and torque settings of about 35 Ncm provide satisfactory results.

Figure 3:
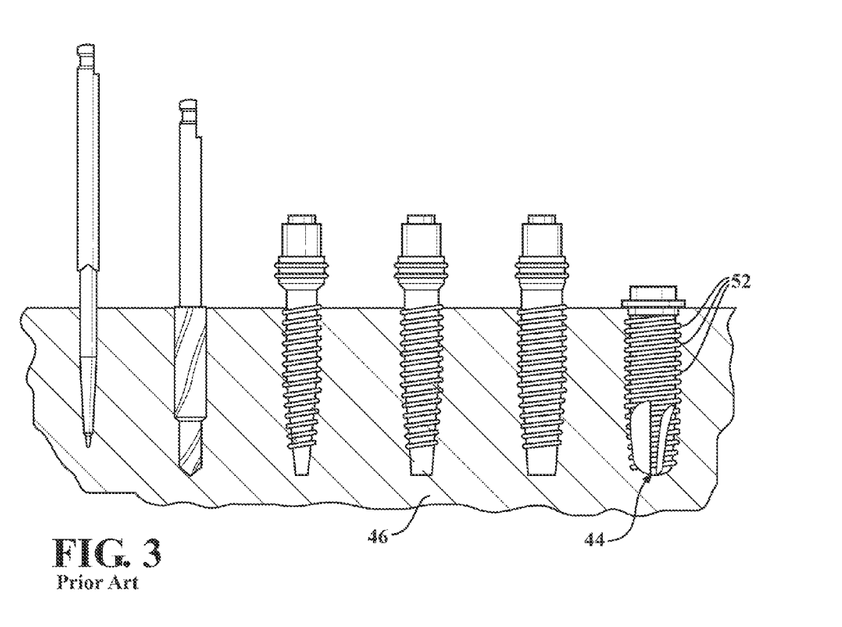
FIG. 3 is a view as in FIG. 2 but showing prior art expander screw tap technique which has seeks to replace the mallet-driven osteotome technique of FIG. 2.
Figure 4:
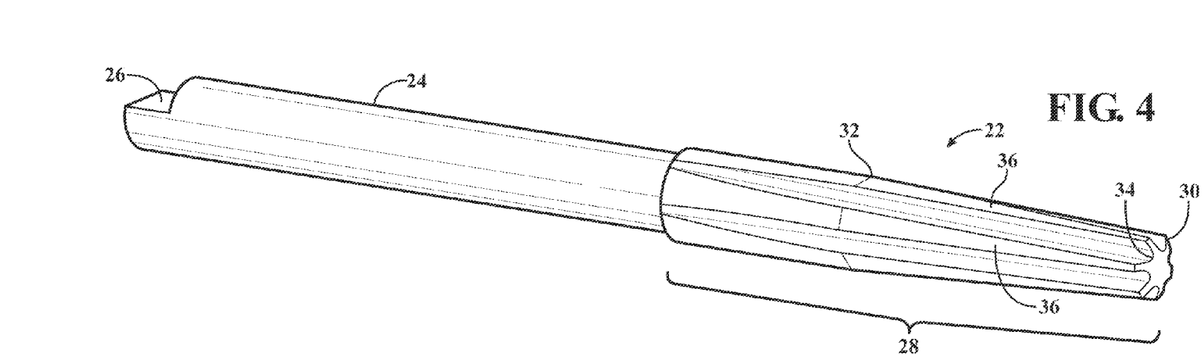
FIG. 4 is a perspective view of an osteotome according to one embodiment of the present invention.
Figure 20:
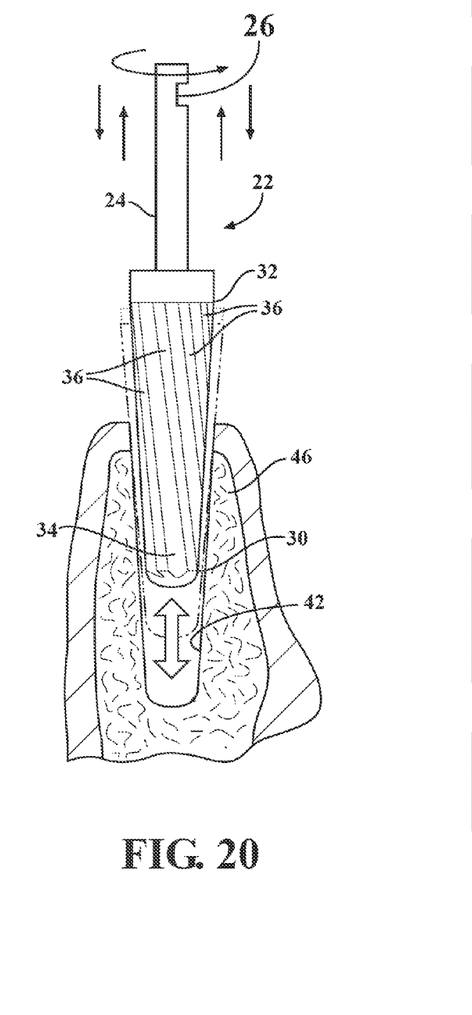
FIG. 20 is a simplified cross-sectional view showing a surgical procedure referred to herein as "bounce" where an osteotome according to the present invention is repeatedly pushed into the osteotomy and withdrawn while the osteotome remains spinning in a repetitive manner so as to enlarge the osteotomy while enabling the surgeon to manage heat build-up and make adjustments on-the-fly.
Figure 21:
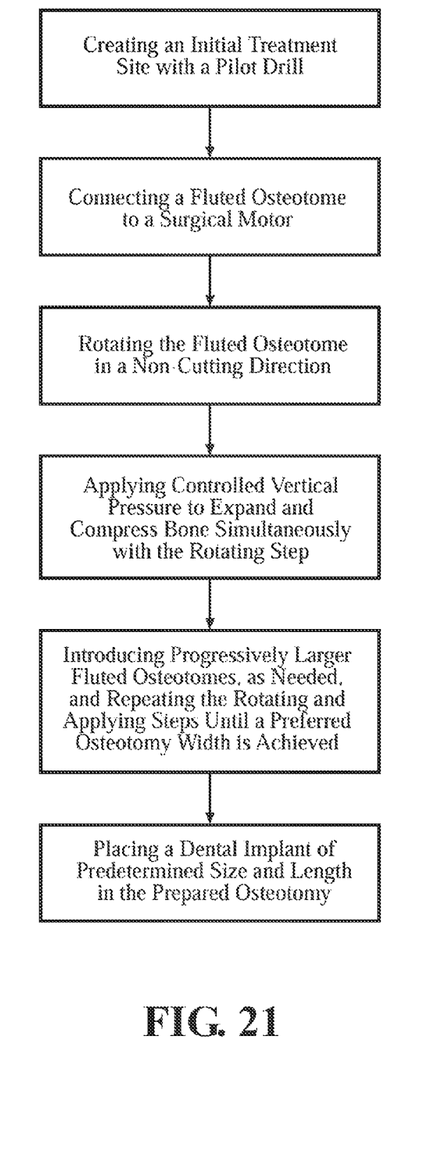
FIG. 21 is a simplified flow chart depicting the primary steps in the subject method.

As perhaps best shown in FIG. 20, the enlarging step may include the controlled practice of bouncing the burnishing edges 40 into and out of contact with the interior surface of the osteotomy 42 while continuously rotating the osteotome 22. This practice is unachievable using prior art osteotome tools and techniques (as shown in FIGS. 2, 3 and 12). However, because the subject osteotome 22 has a tapered working end 22 and only the burnishing edges 40 are ever in contact with the interior surface of the osteotomy 42, the surgeon may at any time lift the working end 28 out of contact to evaluate progress, manage heat, irrigate, adjust approach, or make other corrections. In fact, the surgeon may practice a very controlled technique whereby the burnishing edges 40 are repeated and successively pushed into and pulled out of the osteotomy 42 in a sort of bouncing maneuver. Although this bouncing technique is not required for proper execution of the method, the novel tool shape and other features of this invention enable the bouncing technique if and whenever the surgeon warrants.

It should also be mentioned that if the surgeon warrants, the osteotome 22 may be rotated in the opposite direction (e.g., clockwise in these examples) and utilize the osteotome 22 to enlarge the osteotomy 42 by cutting or excavating bone material from the osteotomy 42 rather than via compression and plastic deformation.

When the full length (approximately 11-15 mm) of the working end 28 has been advanced into the osteotomy, the resultant effect is an incremental expansion of the osteotomy 42 to the dimensions of the working end 28 with little to no removal of bone material 46. The first osteotome 22 is then removed from the osteotomy 42 to reveal a first enlarged osteotomy 42. The first enlarged osteotomy 42 is fully prepared and ready to receive the implant 44 if, in this example with the given dimensions, the fixture portion is sized at about a 3.0 mm diameter.

Figure 16A:
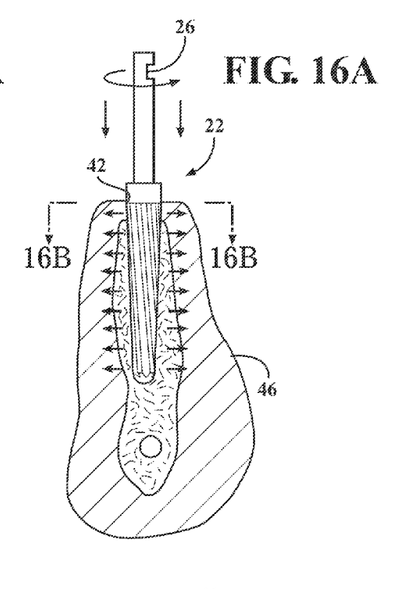
FIG. 16A shows a further progression in the surgical procedure from that of FIG. 15A in which a second osteotome is inserted into the osteotomy and operated in a manner so as to expand the osteotomy further.
Figure 16B:
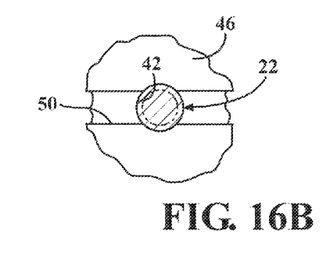
FIG. 16B is a view as taken generally along lines 16B-16B in FIG. 16A.

If the fixture portion of the implant 44 is larger than 3.0 mm (continuing with this example for purposes of illustration), then the first enlarged osteotomy 42 must be enlarged still further. This is accomplished by repeating the inserting and enlarging steps with progressively larger tapered osteotomes 22, as needed, until an osteotomy 42 of predetermined size is achieved. More specifically, as shown in FIG. 16A, a second osteotome 22 having a tapered working end 28 that is larger in diameter than the first osteotome 22, is operatively connected to the surgical motor (not shown). The tapered working end 28 of the second osteotome 22 is inserted into the first enlarged osteotomy 42. Using the previously described exemplary dimensions, the major diameter of the working end 28 of the second osteotome 22 adjacent the leading distal tip 30 is 2.5 mm so that it follows easily the first enlarged osteotomy 42. Because of the widening taper, the major diameter of the working end 28 adjacent upper end 32 is, for example, 3.5 mm. At these exemplary dimensions, the second osteotome 22 having eight equally spaced flutes 36/burnishing edges 40 of straight or helical twist has been found to provide satisfactory results. More or fewer flutes 36/burnishing edges 40 are certainly possible.

The surgeon proceeds to further enlarge the first enlarged osteotomy 42 by forcibly advancing the second osteotome 22 into the first enlarged osteotomy 42 to create a second enlarged osteotomy 42. As before, the advancing step is comprised of simultaneously rotating and pushing the working end 28 of the second tapered osteotome 22 into the osteotomy 42 so that its one or more burnishing edges 40 concentrate the pushing and rotational force in outward normal and tangential component forces (FIG. 8) against the interior surface of the osteotomy 42. When the full length (approximately 11-15 mm) of the working end 28 has been advanced into the osteotomy 42, the second osteotome 22 is then removed from the osteotomy 42 to reveal a second enlarged osteotomy 42. The second enlarged osteotomy 42 is fully prepared and ready to receive the implant 44 if, in this example with the given dimensions, the fixture portion is sized at about a 4.0 mm diameter.

Figure 17A:
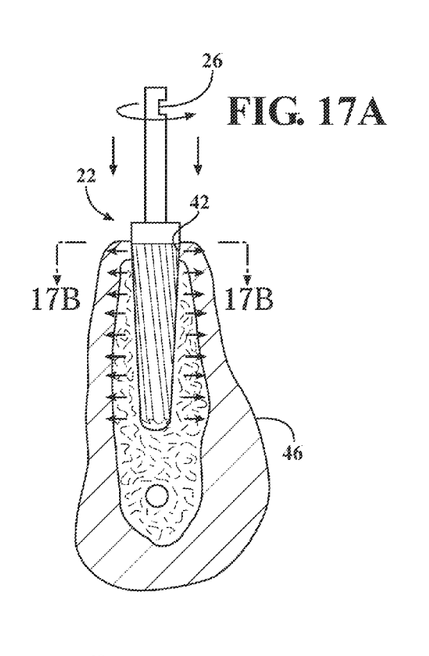
FIG. 17A shows a further progression in the expansion process from that depicted in FIGS. 14A and 15A and 16A.
Figure 17B:
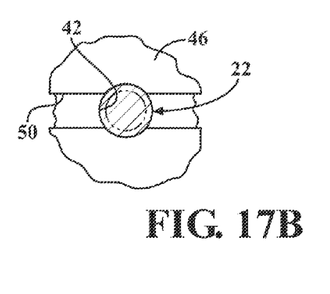
FIG. 17B is a view taken from lines 17B-17B in FIG. 17A.

If the fixture portion of the implant 44 is larger than 4.0 mm (continuing with this example for purposes of illustration), then the second enlarged osteotomy 42 must be enlarged still further. This is accomplished by repeating the inserting and enlarging steps with a progressively larger tapered osteotome 22. FIG. 17A illustrates this scenario where a third osteotome 22 is operatively connected to the surgical motor. Its tapered working end 28 is inserted into the second enlarged osteotomy 42. Using the previously described exemplary dimensions, the major diameter of the third osteotome 22 adjacent its leading distal tip 30 is 3.5 mm, and adjacent its upper end 32 may, for example, be 4.5 mm. At these exemplary dimensions, the third osteotome 22 may have ten equally spaced flutes 36/burnishing edges 40 of straight or helical twist, although more or fewer flutes 36/burnishing edges 40 are certainly possible.

The surgeon proceeds to further enlarge the second enlarged osteotomy 42 by simultaneously rotating and pushing the working end 28 of the third tapered osteotome 22 into the osteotomy 42 so that its one or more burnishing edges 40 concentrate the pushing and rotational force in outward normal and tangential component forces (FIG. 8) against the interior surface of the osteotomy 42. When the full length (approximately 11-15 mm) of the working end 28 has been advanced into the osteotomy 42, the third osteotome 22 is then removed from the osteotomy 42 to reveal a third enlarged osteotomy 42. The third enlarged osteotomy 42 is fully prepared and ready to receive the implant 44 if, in this example with the given dimensions, the fixture portion is sized at about a 5.0 mm diameter.

Figure 18A:
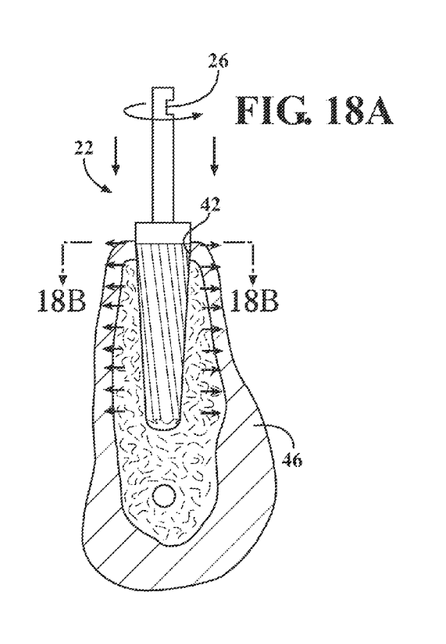
FIG. 18A shows a further progression in the expansion process from that depicted in FIGS. 14A and 15A and 16A.
Figure 18B:
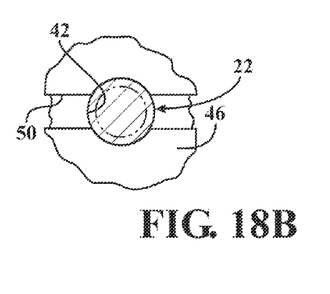
FIG. 18B is a view taken from lines 18B-18B in FIG. 18A.

If the fixture portion of the implant 44 is larger than 5.0 mm (continuing with this example for purposes of illustration), then the third enlarged osteotomy 42 must be enlarged still further. This is accomplished by repeating the inserting and enlarging steps with a progressively larger tapered osteotome 22. FIG. 18A illustrates use of a fourth osteotome 22 having (for example) a major diameter adjacent its leading distal tip 30 of 4.5 mm, and adjacent its upper end 32 of 5.5 mm. At these exemplary dimensions, the fourth osteotome 22 may have twelve equally spaced flutes 36/burnishing edges 40 of straight or helical twist, although more or fewer flutes 36/burnishing edges 40 are certainly possible.

The surgeon proceeds to further enlarge the third enlarged osteotomy 42 by simultaneously rotating and pushing the working end 28 of the fourth tapered osteotome 22 into the osteotomy 42. As before, the one or more burnishing edges 40 concentrate the pushing and rotational forces against the interior surface of the osteotomy 42. When the full length (approximately 11-15 mm) of the working end 28 has been advanced into the osteotomy 42, the fourth osteotome 22 is then removed from the osteotomy 42 to reveal a fourth enlarged osteotomy 42. The fourth enlarged osteotomy 42 is fully prepared and ready to receive the implant 44 if, in this example with the given dimensions, the fixture portion is sized at about a 6.0 mm diameter.

Figure 19A:
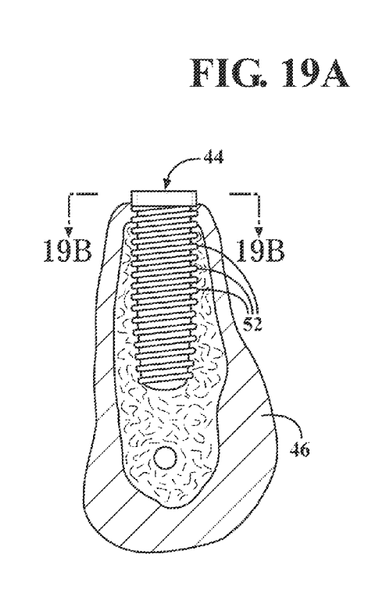
FIG. 19A is a cross-sectional view of the region as in FIG. 18A showing the installation of an implant into the fully enlarged prepared osteotomy.
Figure 19B:
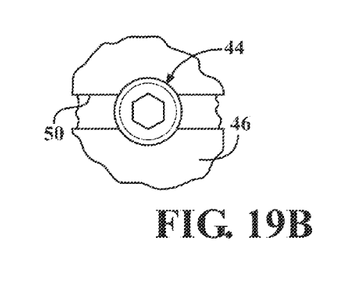
FIG. 19B is a view as taken along lines 19B-19B in FIG. 19A.

To complete the example, FIG. 19A shows the 6.0 mm diameter fixture portion of an implant 44 installed into the fourth enlarged osteotomy 42. The step of installing a fixture portion of an implant 44 includes directly engaging an exterior anchoring thread form 52 of the fixture portion into the expanded osteotomy formed by the burnishing edge 40.

The surgical method of this invention, and in particular the diameter to which the osteotomy 42 can be ultimately expanded, is of course limited by the physical properties of the bone 46 and other factors. In other words, the steps of expanding as described herein are directly related to the final desired fixture 44 diameter but also related to the ability of the bone 46 to plastically deform (via the above-described microcracks) without fracturing. For example, in some conditions it is not possible for even a skilled surgeon to take a 3 mm width of bone 46 and use the procedures of this invention to expand an osteotomy 42 all the way to 5.5 mm without fracturing the bone 46. However, it may be possible to expand the osteotomy 42 to a slightly smaller 4.5 mm so that it will receive a 5 mm diameter implant 44. Thus, it should be understood that bone's ability to plastically deform without fracturing dictates how much expansion can be achieve, and also dictates at which step the surgeon must to stop the expansion process to avoid fracturing the bone 46.

The surgical method of this invention enables an expansion of an initial osteotomy 42 to receive a dental implant 44 that is significantly less traumatic than other prior art osteotome techniques, that is faster than other prior art osteotome techniques, that is able to rear previously difficult to reach areas (e.g., the lower mandible posterior), that requires fewer progressive steps (and tools) to achieve a final enlarged osteotomy than other prior art osteotome techniques, and that is significantly better at managing heat build-up than other prior art osteotome techniques. Heat management is enhanced through irrigation into the osteotomy (difficult with prior art techniques) and also by maintaining a separation space between the root shaft 34 and the bone interior surface of the osteotomy 42. This separation space means less friction and also the opportunity for some degree of convective cooling.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A surgical method for expanding an initial osteotomy to receive a dental implant using continuous high-speed rotation, said method comprising the steps of:
   providing a rotary osteotome having a tapered working end, the working end having a plurality of longitudinally extending burnishing edges;
   positioning the tapered working end of the osteotome over an open end of an initial osteotomy, the initial osteotomy having an interior surface surrounded by bone and a bottom end;
   rotating the working end of the osteotome at high speed;
   enlarging the initial osteotomy by forcibly advancing the rotating working end into the initial osteotomy toward the bottom end so that the burnishing edges lap against the interior surface of the initial osteotomy without cutting into the surrounding bone to form an expanded osteotomy, the rate of said enlarging step being independent of the rate of rotation of the working end;
   and irrigating the initial osteotomy concurrently with said enlarging step.

2. The surgical method of claim 1, wherein the working end of the osteotome includes a plurality of flutes extending from a root shaft, and wherein said enlarging step includes maintaining a separation space between the root shaft and the bone interior surface of the osteotomy.

3. The surgical method of claim 2, wherein the plurality of flutes correspond in number to the plurality of burnishing edges, each flute extends radially outwardly to a crest defining the major diameter of the osteotome, each burnishing edge disposed along the crest of a respective one of the flutes, and said enlarging step further including manually applying variable axial pressure.

4. The surgical method of claim 2, wherein the plurality of burnishing edges are non-rotatably fixed relative to the root shaft.

5. The surgical method of claim 2, wherein the plurality of burnishing edges are each defined by a large negative rake angle.

6. The surgical method of claim 1, wherein said enlarging step includes rotating the working end of the osteotome at speeds greater than 200 RPM.

7. The surgical method of claim 1, wherein said enlarging step includes applying a torque to the working end of the osteotome greater than 15 Ncm.

8. The surgical method of claim 1, wherein said enlarging step includes axially reciprocating the plurality of burnishing edges into and out of contact with the interior surface of the osteotomy while continuously rotating the osteotome and progressively advancing the working end deeper into the osteotomy.

9. The surgical method of claim 1, wherein the osteotome is a first osteotome and has a predetermined number of the plurality of burnishing edges, and providing a second larger tapered osteotome having a greater number of burnishing edges than the predetermined number of the first osteotome.

10. The surgical method of claim 1, further including installing a fixture portion of a dental implant into the expanded osteotomy, wherein said step of installing a fixture portion includes directly engaging an exterior anchoring thread form of the fixture portion into the expanded osteotomy formed by the plurality of burnishing edges.

11. The surgical method of claim 1, wherein the plurality of burnishing edges each have a spiral twist along the length of the working end.

12. The surgical method of claim 1, wherein the plurality of burnishing edges each have a generally straight configuration along the length of the working end.

13. The surgical method of claim 1, further including the step of preparing an initial osteotomy site by drilling a pilot hole into the bone, the pilot hole comprising the initial osteotomy.

14. The surgical method of claim 13, wherein said step of preparing an initial osteotomy site includes sawing a groove along the bone, the sawed groove intersecting the pilot hole or the pilot hole intersecting the sawed groove depending on the order of the surgical steps.

15. A surgical method for enlarging an osteotomy to receive a dental implant, said method comprising the steps of:
   providing an osteotome having a tapered working end, the working end including a plurality of burnishing edges,
   positioning the working end of the osteotome over an open end of an osteotomy, the osteotomy having an interior surface surrounded by bone, and
   progressively advancing the working end of the osteotome into the osteotomy by continuously rotating the working end at speeds greater than 200 RPM while axially reciprocating the burnishing edges into and out of contact with the interior surface of the osteotomy.

16. The method of claim 15, further including irrigating the osteotomy concurrently with said progressively advancing step.

17. The method of claim 15, wherein said progressively advancing step includes lapping the burnishing edges against the interior surface of the osteotomy without cutting into the surrounding bone, and wherein the rate of advance is independent of the rate of rotation of the working end.

\* \* \* \* \*